United States Patent
Faoro et al.

(10) Patent No.: US 7,527,630 B2
(45) Date of Patent: May 5, 2009

(54) APPARATUS FOR THE PREPARATION OF A FEMORAL CONDYLE

(75) Inventors: Francisco Faoro, Zürich (CH); Tom Overes, Winterthur (CH)

(73) Assignee: Zimmer, GmbH, Winterthur (CH)

( * ) Notice: Subject to any disclaimer, the term of this patent is extended or adjusted under 35 U.S.C. 154(b) by 611 days.

(21) Appl. No.: 10/823,031

(22) Filed: Apr. 13, 2004

(65) Prior Publication Data

US 2004/0249387 A1   Dec. 9, 2004

(30) Foreign Application Priority Data

Apr. 25, 2003   (EP)   ................... 03009439

(51) Int. Cl.
*A61B 17/58*   (2006.01)
(52) U.S. Cl. ........................................ 606/90
(58) Field of Classification Search ............... 606/87, 606/88, 90; 600/201, 222, 184, 185; 254/13, 254/50.1, 88, 92, 98
See application file for complete search history.

(56) References Cited

U.S. PATENT DOCUMENTS

| | | | |
|---|---|---|---|
| 3,532,088 A * | 10/1970 | Fiore ........................... 600/213 |
| 4,349,018 A | 9/1982 | Chambers |
| 4,524,766 A | 6/1985 | Petersen |
| 4,566,448 A | 1/1986 | Rohr, Jr. |
| 4,574,794 A | 3/1986 | Cooke et al. |
| 4,646,729 A | 3/1987 | Kenna et al. |
| 4,738,253 A | 4/1988 | Buechel et al. |
| 4,759,350 A | 7/1988 | Dunn et al. |
| 4,825,857 A | 5/1989 | Kenna |
| 4,841,975 A | 6/1989 | Woolson |
| 4,938,762 A | 7/1990 | Wehrli |
| 5,002,547 A | 3/1991 | Poggie et al. |
| 5,116,338 A * | 5/1992 | Poggie et al. ................. 606/90 |
| 5,122,144 A | 6/1992 | Bert et al. |
| 5,213,112 A * | 5/1993 | Niwa et al. ................... 600/587 |
| 5,234,433 A | 8/1993 | Bert et al. |
| 5,306,276 A | 4/1994 | Johnson et al. |
| 5,342,367 A | 8/1994 | Ferrante et al. |
| 5,344,423 A | 9/1994 | Dietz et al. |
| 5,364,401 A | 11/1994 | Ferrante et al. |

(Continued)

FOREIGN PATENT DOCUMENTS

DE   203 03 498 U1   8/2003

(Continued)

*Primary Examiner*—Eduardo C Robert
*Assistant Examiner*—Michael J Araj
(74) *Attorney, Agent, or Firm*—Baker & Daniels LLP

(57) ABSTRACT

The invention relates to an apparatus for the preparation of a femoral condyle for the insertion of monocondylar knee implants, comprising a spreading device for the setting of a desired spacing between a femoral condyle and an oppositely disposed tibia plateau and comprising at least one functional attachment couplable in a vertically adjustable manner with the spreading device, wherein the spreading device includes a spreading section, which can be introduced between the femoral condyle and the tibia plateau and which extends substantially perpendicular to the spreading direction, and a handling section for the spreading section which includes an angle α>90° with the spreading section (27, 29), and wherein the functional attachment supports a cutting and/or drilling jig and is adjustable at least vertically relative to the spreading device when the desired spacing is set at the handling section by means of the spreading device.

20 Claims, 9 Drawing Sheets

U.S. PATENT DOCUMENTS

Figure 1:
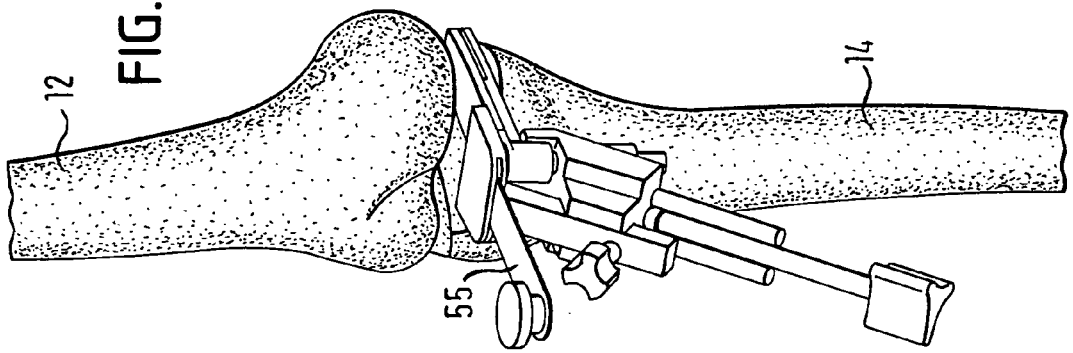

| | | | |
|---|---|---|---|
| 5,364,402 A | 11/1994 | Mumme et al. | |
| 5,368,552 A | 11/1994 | Williamson et al. | |
| 5,445,640 A | 8/1995 | Johnson et al. | |
| 5,458,645 A | 10/1995 | Bertin | |
| 5,527,316 A | 6/1996 | Stone et al. | |
| 5,540,696 A * | 7/1996 | Booth et al. | 606/88 |
| 5,601,563 A | 2/1997 | Burke et al. | |
| 5,611,802 A | 3/1997 | Samuelson et al. | |
| 5,628,750 A | 5/1997 | Whitlock et al. | |
| 5,643,272 A | 7/1997 | Haines et al. | |
| 5,681,320 A | 10/1997 | McGuire | |
| 5,683,397 A | 11/1997 | Vendrely et al. | |
| 5,688,280 A | 11/1997 | Booth, Jr. | |
| 5,704,941 A | 1/1998 | Jacober et al. | |
| 5,788,700 A | 8/1998 | Morawa et al. | |
| 5,800,438 A * | 9/1998 | Tuke et al. | 606/90 |
| 5,824,085 A | 10/1998 | Sahay et al. | |
| 5,860,980 A * | 1/1999 | Axelson et al. | 606/88 |
| 5,911,723 A * | 6/1999 | Ashby et al. | 606/88 |
| 6,051,016 A | 4/2000 | Mesaros et al. | |
| 6,090,114 A | 7/2000 | Matsuno et al. | |
| 6,296,646 B1 | 10/2001 | Williamson | |
| 6,475,228 B1 | 11/2002 | Mesaros et al. | |
| 6,478,799 B1 | 11/2002 | Williamson | |
| 6,503,254 B2 | 1/2003 | Masini | |
| 6,575,980 B1 | 6/2003 | Robie et al. | |
| 6,632,225 B2 | 10/2003 | Sanford et al. | |
| 6,695,848 B2 | 2/2004 | Haines | |
| 7,094,241 B2 | 8/2006 | Hodorek et al. | |
| 7,235,080 B2 * | 6/2007 | Hodorek | 606/87 |
| 7,335,206 B2 | 2/2008 | Steffensmeier et al. | |
| 2002/0198530 A1 | 12/2002 | Sanford et al. | |
| 2003/0100906 A1 | 5/2003 | Rosa et al. | |
| 2003/0225413 A1 | 12/2003 | Sanford et al. | |
| 2003/0233149 A1 | 12/2003 | Hodorek | |
| 2004/0249387 A1 | 12/2004 | Faoro | |
| 2005/0070910 A1 | 3/2005 | Keene | |
| 2006/0030855 A1 | 2/2006 | Haines | |
| 2006/0195111 A1 | 8/2006 | Couture | |
| 2006/0247647 A1 | 11/2006 | Hodorek et al. | |

FOREIGN PATENT DOCUMENTS

| | | |
|---|---|---|
| EP | 0 709 061 A1 | 5/1996 |
| EP | 0 809 969 A2 | 12/1997 |
| EP | 0839501 B1 | 5/1998 |
| EP | 1424042 B1 | 6/2004 |
| FR | 02648699 A1 | 12/1990 |
| FR | 2 679 766 | 2/1993 |
| FR | 02819168 A1 | 4/2002 |
| WO | WO 01/66021 A1 | 9/2001 |
| WO | WO 01/85038 A1 | 11/2001 |

* cited by examiner

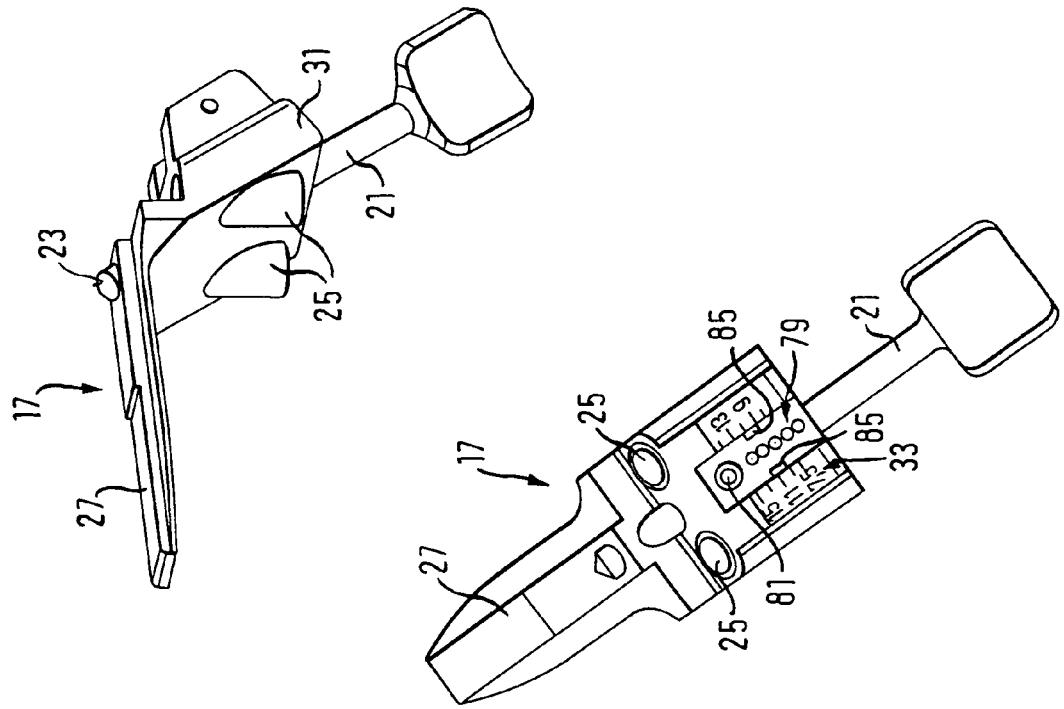
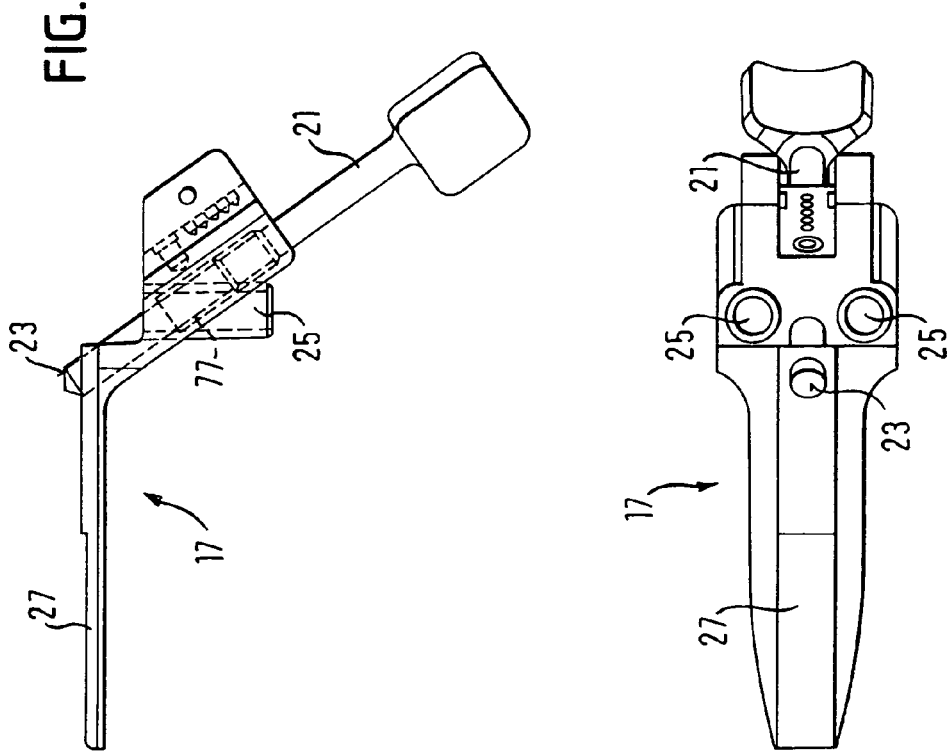
FIG. 6

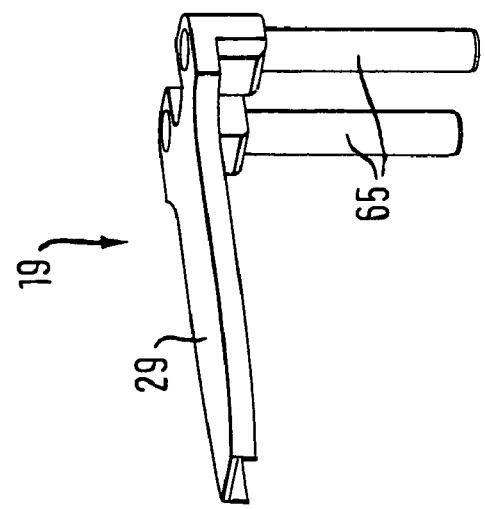
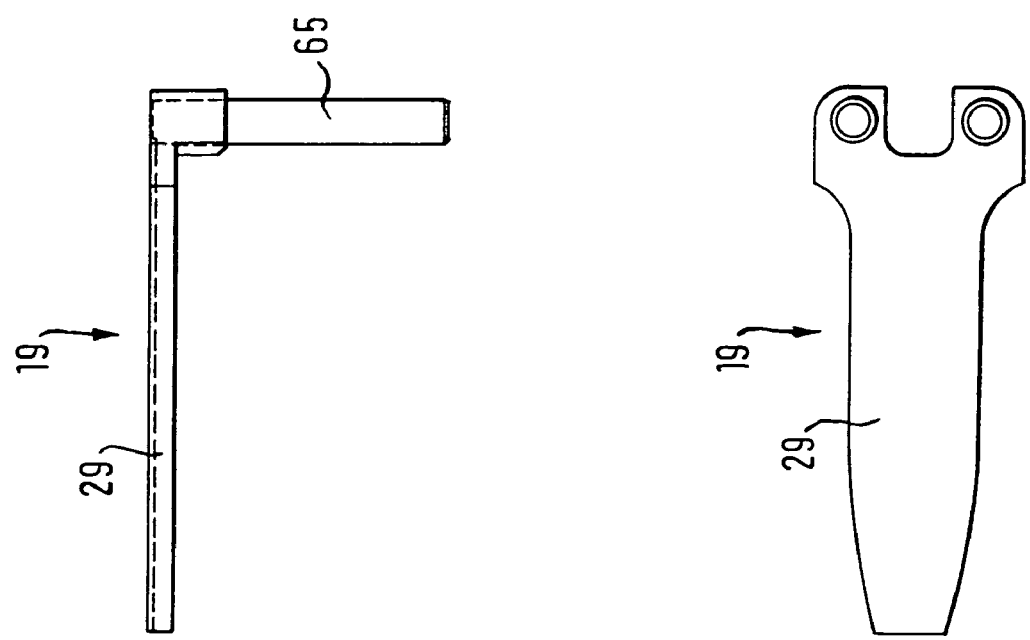
FIG. 7

APPARATUS FOR THE PREPARATION OF A FEMORAL CONDYLE

CROSS-REFERENCE TO RELATED APPLICATION

This application claims priority of EPO Patent Application No. 03 009 439.5 filed Apr. 25, 2003.

The invention relates to an apparatus for the preparation of a femoral condyle for the insertion of monocondylar knee implants.

When monocondylar, i.e. one-sided, knee prostheses are inserted, the condyles of the tibia and of the femur must be prepared in order to create contact surfaces on the bone which ensure a defined position of the tibia and femur implants.

The contact surfaces are produced by cutting away bone material at the condyles. In this process, one endeavors to remove as little bone material as possible. Furthermore, care must be taken that the cut surfaces at the tibia and at the femur are correctly oriented relative to one another so that the tibia and femur implants can cooperate in a manner corresponding to the natural movement of the remaining, healthy side of the knee joint.

When, in the course of a knee operation, the tibia is prepared first and, in this process, a tibia plateau is produced onto which a tibia implant is later mounted, it is important on the preparation of the corresponding femoral condyle that the cut surfaces to be produced on the femoral condyle are correctly aligned relative to the cut surfaces produced at the tibia plateau.

It is the object of the invention to provide an apparatus of the initially named kind with which a femur implant can be implanted at the femur in a manner which is as simple and as reliable as possible in the correct position relative to the tibia with an accuracy which is as high as possible.

This object is satisfied by the features of claim 1 and in particular in that the apparatus includes a spreading device for the setting of a desired spacing between a femoral condyle and an oppositely diposed tibia plateau as well as at least one functional attachment vertically adjustably couplable to the spreading device, with the spreading device including a spreading section which can be introduced between the femoral condyle and the tibia plateau and extending substantially perpendicular to the spreading device and a handling section for the spreading section which includes an angle $\alpha > 90°$ with the spreading section, and with the functional attachment supporting a cutting and/or drilling jig and being at least vertically adjustable relative to the spreading direction with the desired spacing being set at the handling section by means of the spreading device.

By spreading open the knee, i.e. by enlarging the spacing between the femur and the tibia, the femur and the tibia can be brought into their natural relative position during the knee operation, with this natural relative position being able to be determined by the surgeon with reference to the natural tension of the ligaments.

The invention makes it possible to position the cutting and/or drilling jig serving for the preparation of the femoral condyle at the right spacing from the previously produced tibia plateau by means of the functional attachment coupled to the spreading device. In accordance with the invention, the positioning of the cutting and/or drilling jig can consequently take place while simultaneously taking into account the natural relative position between the femur and the tibia as well as the thickness of the tibia implant to be inserted.

The angle of more than 90° between the spreading section and the handling section has the advantage that the handling section extends obliquely to the spreading direction and therefore extends away from the knee of the patient during the operation, whereby the handling is substantially facilitated and more space is available, which has a particularly advantageous effect with monocondylar operations. This apparatus design in accordance with the invention furthermore advantageously promotes minimally invasive surgical procedures.

The angle $\alpha$ between the spreading section and the handling section can lie e.g. in the range from 110° to 130°.

Advantageous embodiments of the invention are recited in the dependent claims, in the description and in the drawing.

The spreading device can include a lower part supportable at the tibia plateau, an upper part adjustably guided at the lower part and an actuation member adjustably held at the lower part which cooperates with the lower part and the upper part such that a setting movement of the actuation member can be translated into a spreading movement of the upper part away from the lower part.

Provision can be made for the upper part to be able to be acted on from below via the actuation member and to be pressed away from the lower part in the spreading direction.

A particularly simple handling ability of the spreading device results when, in accordance with a further embodiment of the invention, the actuation member is adjustable obliquely to the spreading direction and the upper part is adjustable parallel to the spreading direction relative to the lower part.

The actuation member can be provided at its free end with a planar pressure surface which extends parallel to a lower side of the upper part which can be acted on by means of the pressure surface and in particular perpendicular to the spreading direction.

Provision is made in a particularly preferred embodiment for a guide for the upper part extending parallel to the spreading direction and for the region at which the actuation member acts on the upper part to be offset with respect to one another perpendicular to the spreading direction. An accidental canting of the upper part guided in the lower part during the spreading procedure is hereby reliably avoided.

The lower part and the upper part can each have a plate-shaped spreading tongue with which the lower part is supported at the tibia plateau and presses the upper part toward the femoral condyle.

Furthermore, provision can be made for the actuation member to be drivable into the intermediate space between the two spreading tongues and toward the lower side of the spreading tongue of the upper part, with the lower part including a base section which extends obliquely to its spreading tongue and in which the guide for the upper part is formed and the actuation member is held.

The actuation member can be made as an adjustable screw such that a screwing movement of the adjustable screw is converted into a linear spreading movement. The transmission ratio can generally be pre-set as desired by a corresponding selection of the thread.

Furthermore, provision can be made in accordance with the invention for the spreading device to be provided with a display device, in particular in the form of a scale, by means of which a desired height of the functional attachment dependent on the thickness of the tibia implant to be inserted can be read off at the spreading device.

Depending on the thickness of the tibia implant to be inserted in accordance with the surgery plan, the correct height of the functional attachment and thus of the cutting and/or drilling jig can be precisely set in this manner.

An advantageous alignment of the functional attachment and thus of the cutting and/or drilling jig relative to the femur is made possible if, in accordance with a further embodiment of the invention, the spreading device is made such that it is moveable relative to the knee in the condition arranged between the tibia plateau and the femoral condyle. The degrees of freedom of movement are in particular a displaceability substantially perpendicular to the spreading direction and/or a rotatability about an axis extending substantially parallel to the spreading direction.

It is furthermore proposed in accordance with the invention for the spreading device to be couplable to a plurality of differently formed functional attachments. This in particular makes it possible to use the spreading device with the knee either in extension or in flexion and to use correspondingly formed functional attachments in each case.

At least one functional attachment can be made as a cutting jig for fixing the position of a condylar cut which is to be carried out when the knee is in extension and which in particular extends substantially parallel to the tibia plateau.

Furthermore, at least one functional attachment can be made as a cutting jig for fixing the position of a condylar cut which is to be carried out when the knee is in flexion and which in particular extends substantially parallel to the tibia plateau.

Provision can furthermore be made for at least one functional attachment to be made as a drilling jig for fixing the position of at least one condylar bore which serves for the fixing of a femur implant, is to be carried out when the knee is in flexion and in particular extends substantially parallel to the tibia plateau.

In a particularly preferred embodiment of the invention, provision is made for at least one functional attachment to be made as a combined cutting and drilling jig for the simultaneous fixing of the position of a condylar cut and of at least one condylar bore when the knee is in flexion.

At least one functional attachment, which is in particular formed as a combined cutting and drilling jig, can be fixable to the femoral condyle.

Furthermore, the functional attachment can include a body section extending obliquely to the spreading direction in the state coupled to the spreading device, being coupled to the spreading device and having a fixing device and a head section fixedly connected to the body section which is formed as a cutting and/or as a drilling jig or as a support for a separate cutting and/or drilling jig.

The head section can be made as a cutting jig with a slot for a cutting tool defining a cutting plane and extending perpendicular to the spreading direction in the state coupled to the spreading device. The cutting tool is in particular the saw blade of a bone saw.

Provision can alternatively be made for the head section to be made as a support for a separate cutting and/or drilling jig which can be releasably connected to the head section and which can be fixed to the femoral condyle when the knee is in flexion. The cutting and/or drilling jig can be adjustable along the head section in the state connected to the head section.

It is furthermore proposed in accordance with the invention that at least one functional attachment, which is in particular made as a combined cutting and drilling jig, can be coupled to an additional cutting jig which is made for the fixing of a further condylar section, in particular when the knee is in flexion, with the further condylar section extending in a curved manner between two planar cut surfaces previously established at the femoral condyle.

The apparatus in accordance with the invention can thus be provided in the form of a multi-functional instrument which can be used with the knee either in extension or in flexion in order to position the cutting and/or drilling jig relative to the femoral condyle to be prepared. This is in particular of advantage when femur implants are used which have a constant thickness. A display device of the spreading device, in particular a display device formed as a scale, can then be used for femoral condylar cuts to be made either in extension or in flexion and extending substantially parallel to the tibia plateau in order to set these condylar cuts in each case in dependence on the thickness of the tibia implant to be inserted.

Figure 8:
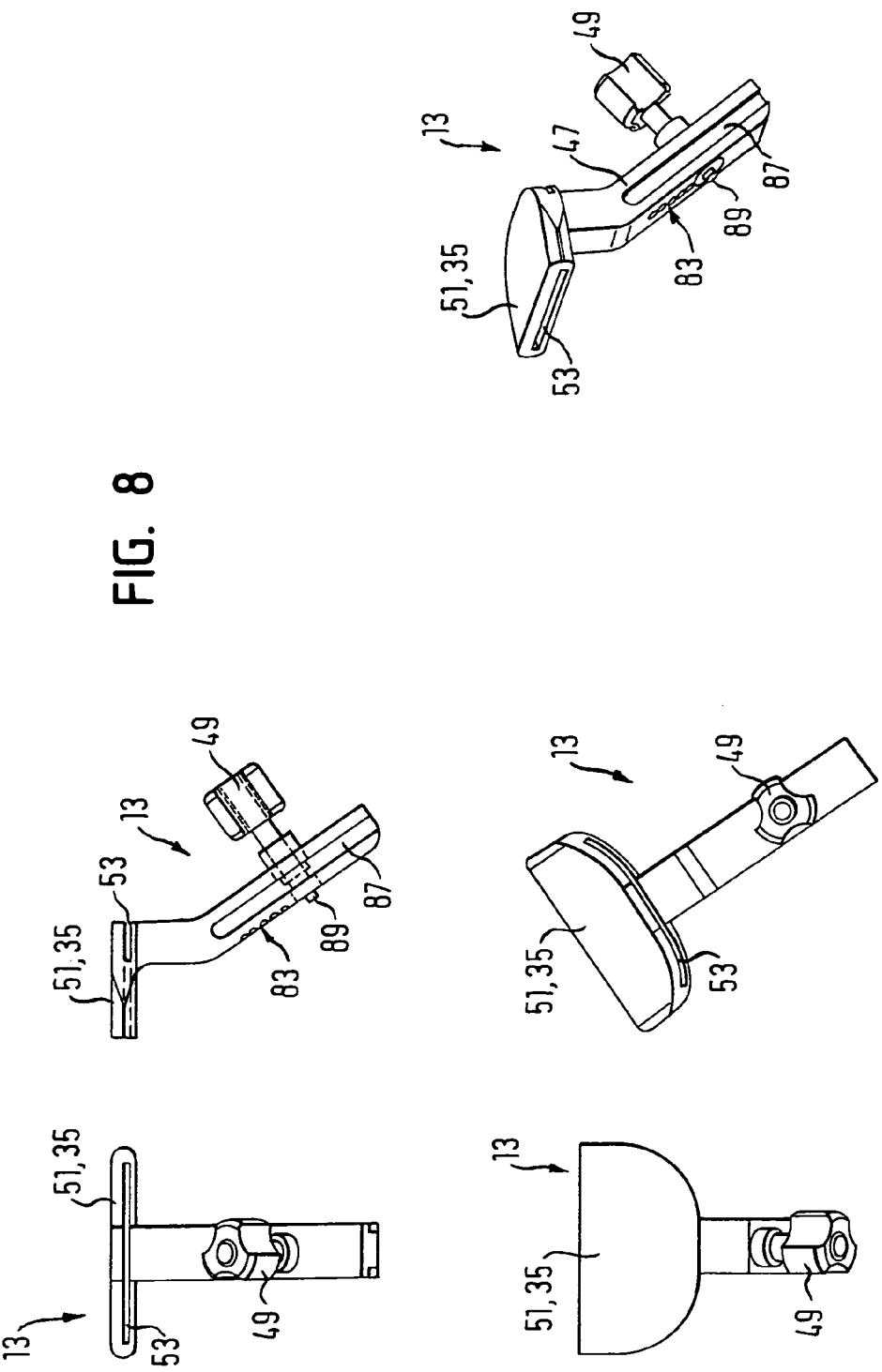
Figure 9:
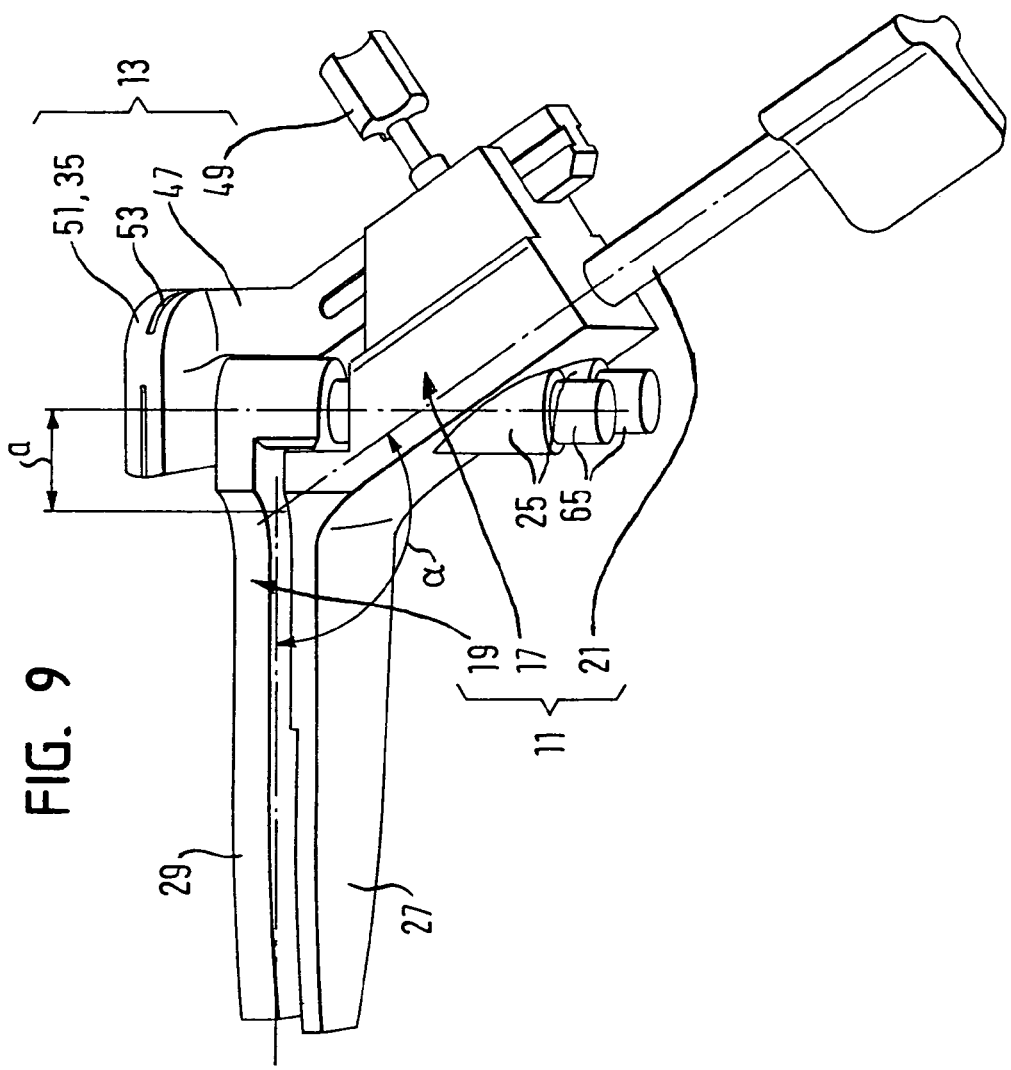
Figure 10:
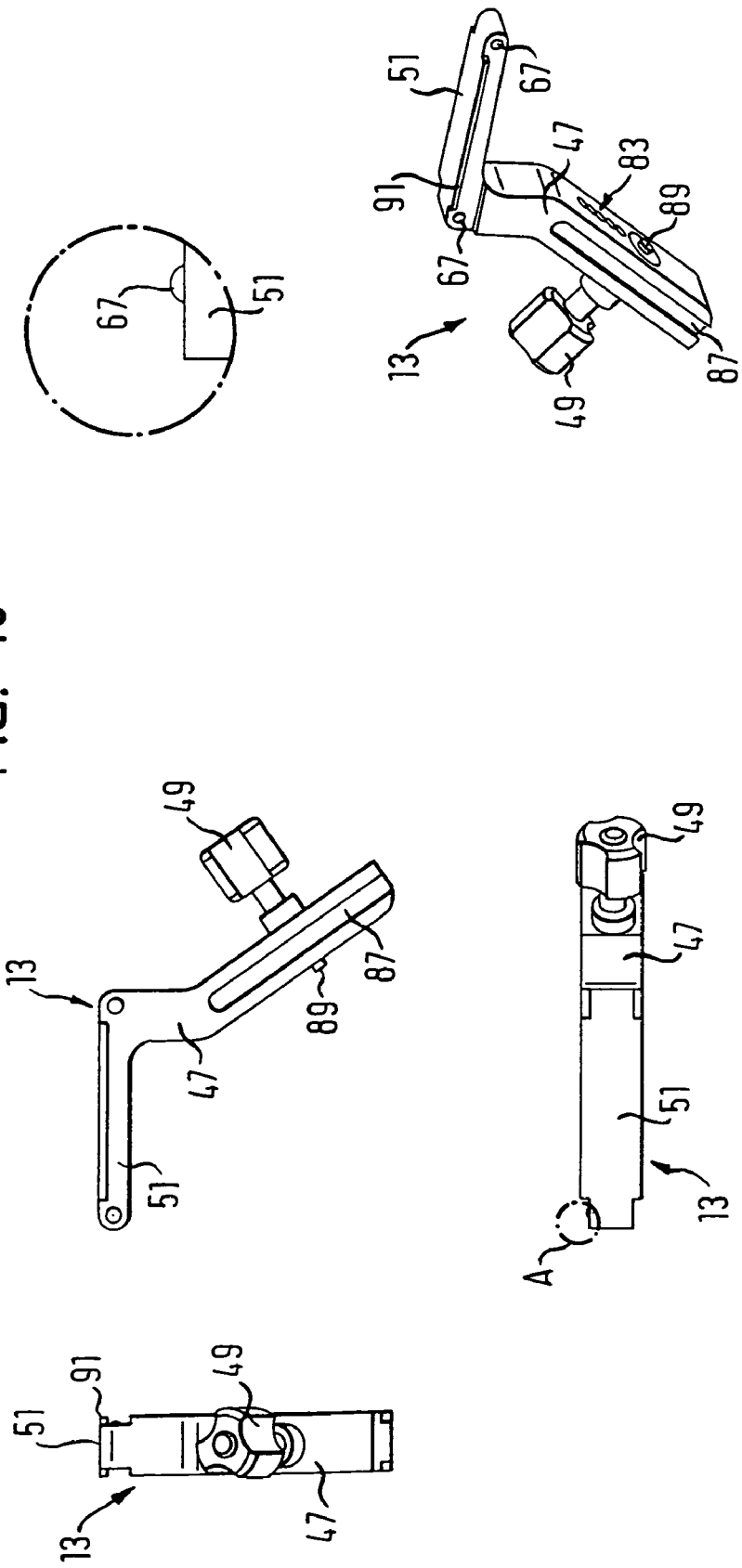
Figure 11:
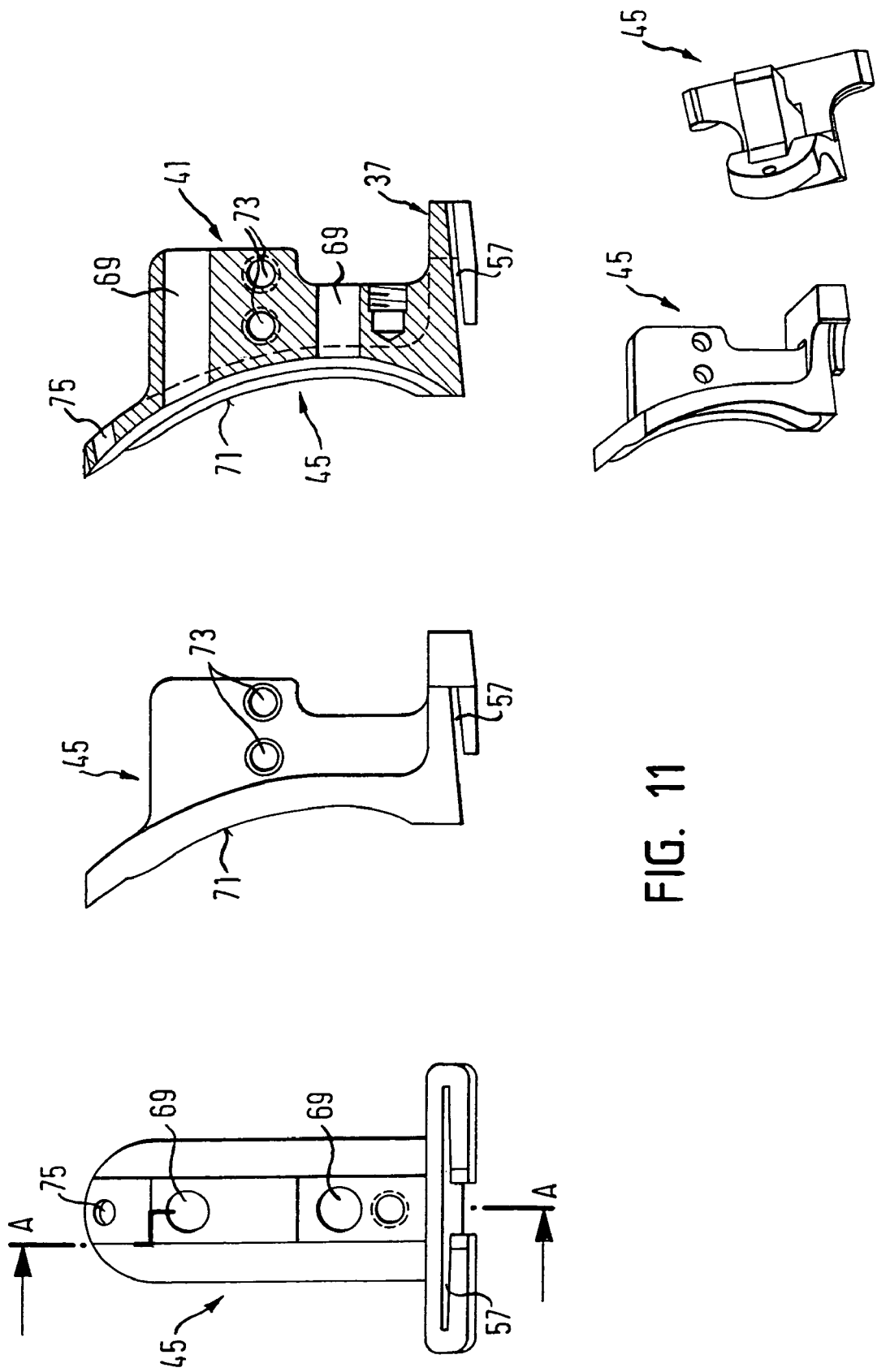

The invention will be described in the following by way of example with reference to the drawing. There are shown:

FIGS. 1 to 5 different phases of part of a knee operation in which a femoral condyle is prepared for the insertion of a femur implant by means of an apparatus in accordance with the invention;

FIGS. 6 and 7 respectively, different views of components of a spreading device in accordance with an embodiment of the invention;

FIG. 8 a functional attachment in accordance with an embodiment of the invention couplable to the spreading device of FIGS. 6 and 7;

FIG. 9 an apparatus in accordance with the invention in the assembled state;

FIG. 10 different views of a part of a further functional attachment in accordance with an embodiment of the invention couplable to the spreading device of FIGS. 6 and 7; and FIG. 11 different views of a combined cutting and drilling jig in accordance with an embodiment of the invention couplable to the functional attachment part of FIG. 10.

Before constructive details of the apparatus in accordance with the invention are considered with reference to FIGS. 6 to 11, that part of a knee operation should first be explained with reference to FIGS. 1 to 5 in which the apparatus in accordance with the invention is used.

The operation in which the apparatus in accordance with the invention is used in accordance with the embodiment shown in the Figures is a uni-compartmental operation in which the tibial condyle and the femoral condyle are prepared either in the lateral compartment or in the medial compartment for insertion of a tibia implant or of a femur implant.

The starting point for that part of the operation in which the apparatus in accordance with the invention is used, is a tibia plateau which is established by two bone cuts extending perpendicular to one another and onto which a tibia implant provided in accordance with the surgery plan and having a specific thickness can be mounted as soon as the oppositely lying femoral condyle has also been prepared with the aid of the apparatus in accordance with the invention for the fixing of a corresponding femur implant.

The set of instruments in accordance with the invention includes, in accordance with the embodiment described in the following, a spreading device 11 which can be coupled to two different functional attachments 13 of which the one is used when the knee is in extension (cf. FIGS. 1 to 3) and the other is used when the knee is in flexion (cf. FIGS. 4 and 5).

The spreading device 11 includes a lower part 17 at which an upper part 19 is adjustably guided in the spreading direction and an actuation member 21 in the form of an adjustable screw is adjustably held. By actuation of the adjustable screw 21, the upper part 19 can be moved upwardly away from the lower part 17 in order to spread open the knee, i.e. to press the femur 12 away from the tibia 14 and thus the femoral condyle still to be prepared away from the already prepared tibia plateau.

The lower part 17 of the spreading device 11 is supported at the previously established tibia plateau, whereas the upper part 19 acts directly on the opposite femoral condyle.

Figure 2:
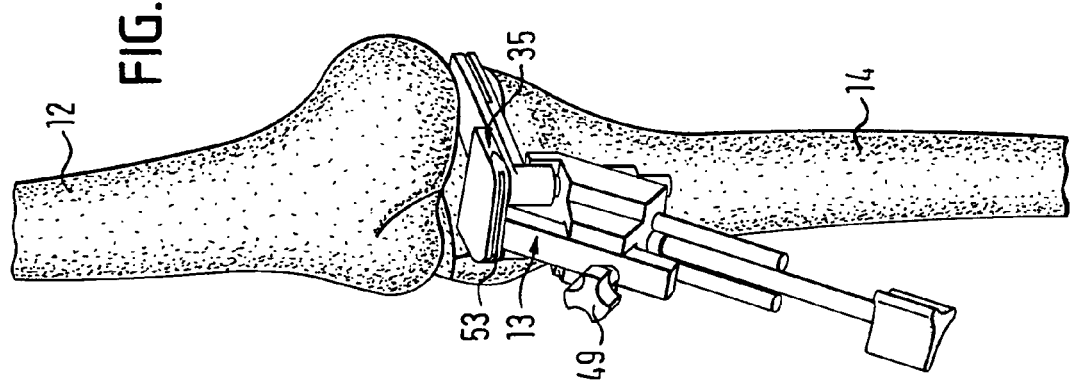
Figure 3:
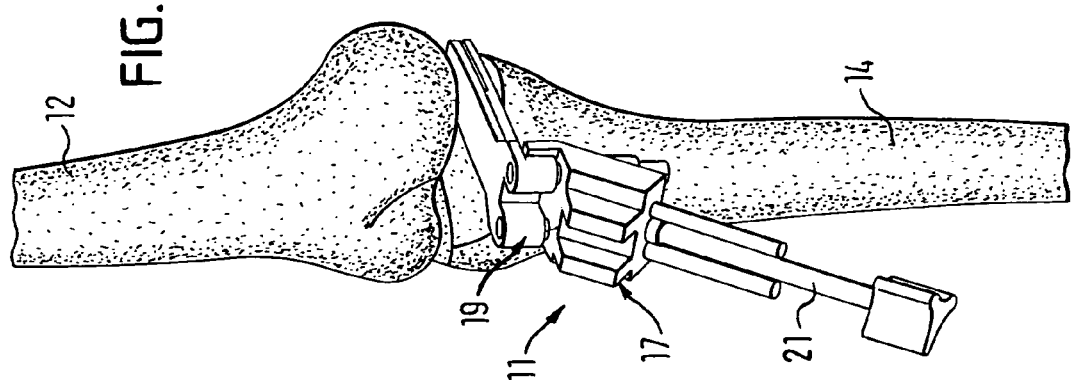
Figure 4:
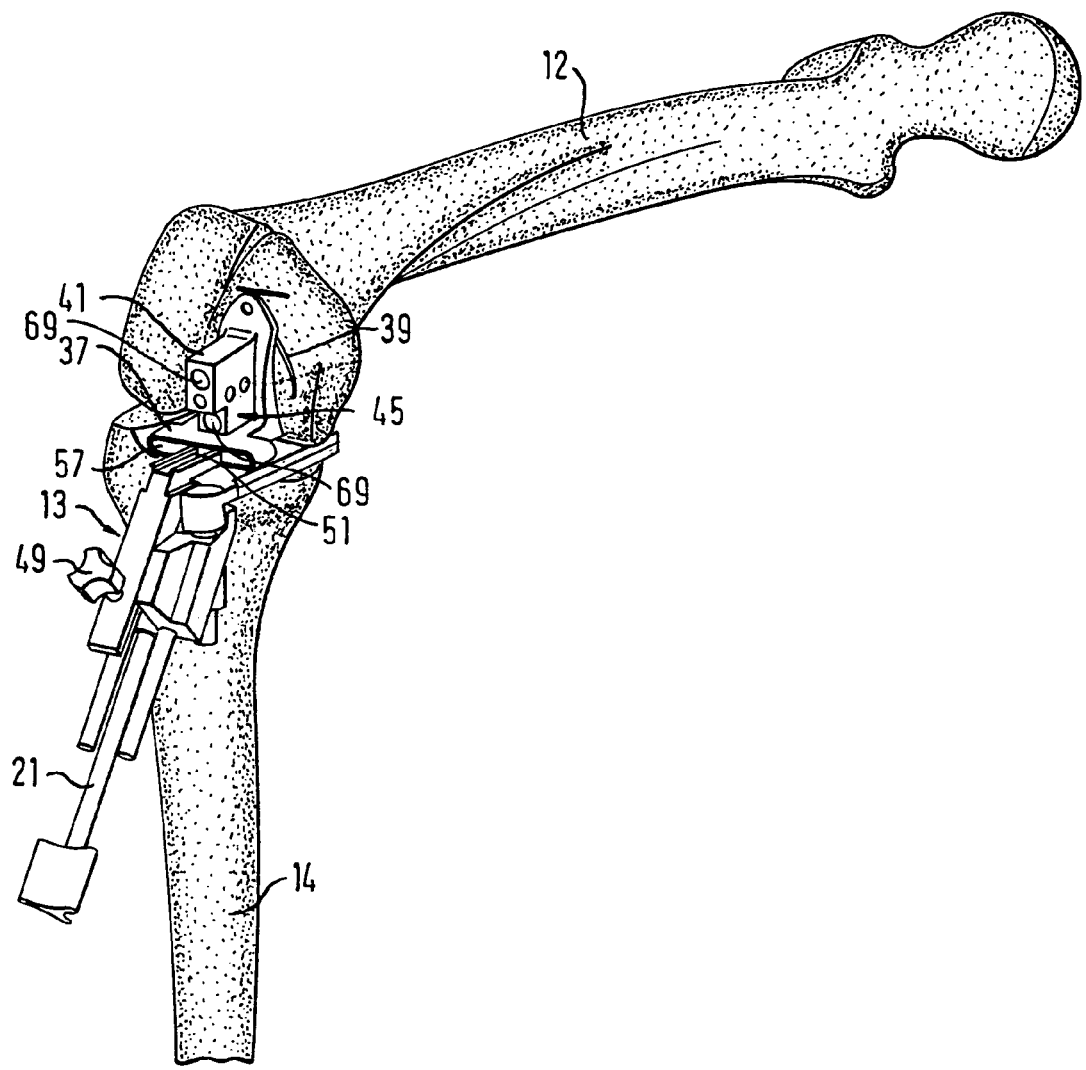

First, in accordance with FIGS. 1 to 3, the knee in extension is spread by actuating the adjustable screw 21 until the natural relative position between the femur 12 and the tibia 14 is reached which the surgeon can recognize by the natural tension of the ligaments.

Subsequently, a functional attachment 13 which is regionally made as a carriage couplable to the lower part 17 of the spreading device 11 and which has a head part formed as a cutting jig 35 with a slot 53 for a saw blade 55 is displaced along the lower part 17 and thus obliquely to the spreading direction until the correct height of the slot 53 of the cutting jig 35 is reached which is dependent on the thickness of the tibia implant to be inserted in accordance with the surgery plan. For this purpose, a scale is attached to the lower part 17 at which the surgeon can read off the reaching of the correct position of the functional attachment 13 and thus of the slot 53. In this position, the functional attachment 13 is fixed to the lower part 17 by means of a fixing device 49.

Subsequently, a first cut extending parallel to the tibia plateau is carried out in the femoral condyle by means of a saw blade 55 guided through the slot 53, with the cut depth being selected such that the femoral condyle is only cut into, but that no part of the bone is completely cut off. Initially, therefore, only a slot is formed in the femoral condyle by means of the saw blade 55.

Before this first condylar cut is carried out, either the functional attachment 13 or the spreading device 11 can be aligned relative to the femur 12 via a control linkage (not shown) so that the first condylar cut is not only carried out in the correct height, but also in the correct position with respect to the direction lateral-medial.

The carrying out of this first femoral condylar cut takes place with the knee spread into its natural position. The coupling of the functional attachment 13 to the lower part 17 can take place before or after the spreading of the knee.

The functional attachment 13 serving for the preparation of the femoral condyle in extension is subsequently removed and replaced by another functional attachment 13 (cf. FIGS. 4 and 5) which serves for the preparation of the femoral condyle with the knee in flexion. In FIGS. 4 and 5, the first condylar cut 39 previously carried out in extension can now be recognized.

The head section 51 of the functional section 13 is made as a support for a separate, combined cutting and drilling jig 45 which includes a section formed as a cutting jig 37 and a section formed as a drilling jig 41. The cutting and drilling jig 45 corresponds with its drilling jig section 41 to the femoral implant to be inserted in accordance with the surgery plan insofar as the curvature of the side of the drilling jig section 41 facing the femoral condyle corresponds to the curvature of the corresponding femur implant side, on the one hand, and passages 69 formed in the drilling jig section 41 correspond with respect to position and orientation with regard to the curved side to the spigots of the femur implant to be inserted, on the other hand.

The combined cutting and drilling jig 45 is present in different sizes with respect to its drilling jig section 41 which correspond to the different existing femur implant sizes.

Furthermore, the combined cutting and drilling jig 45 is longitudinally displaceably arranged on the head section 51 of the functional attachment 13 perpendicular to the spreading direction and can be pushed in this manner up to and onto the femoral condyle with its curved side. Before the jig 45 is fixed to the femoral condyle, it can be aligned relative to the femur 12 by means of an alignment aid (not shown). A movement of the jig 45 relative to the femur 12 is possible in that the spreading device 11 in accordance with the invention is movable relative to the knee in the state arranged between the tibia plateau and the femoral condyle, i.e. with the knee spread open, and indeed both displaceable substantially parallel to the tibia plateau and thus perpendicular to the spreading direction and rotatable about an axis extending perpendicular to the spreading direction.

The fixing of the jig 45 at the femoral condyle takes place in that the jig 45 is first positioned at the femoral condyle by means of a positioning pin 59 and subsequently the femoral condyle is pre-drilled through the fixing passages 69 formed in the drilling jig section 41, whereupon the jig 45 is secured to the femoral condyle by means of screws 61, 63.

Then a second condylar cut is carried out by means of a saw blade 55 guided through the slot 57 formed in the cutting jig section 37 and extends substantially perpendicular to the first condylar cut 39. Part of the bone is completely cut off by the second condylar cut.

The combined cutting and drilling jig 45 itself and its use for the preparation of the femoral condyle are not the subject of the invention so that they are not looked at in more detail in the following. For reasons of completeness, it should still be mentioned that for the further femoral condyle preparation the jig 45 fixed to the femoral condyle is coupled to an additional cutting jig (not shown) which serves to carry out a further condylar cut which extends in a curved manner in accordance with the curvature of the side of the jig 45 facing the femoral condyle and connects the two previously made planar cut surfaces to one another.

Figure 5:
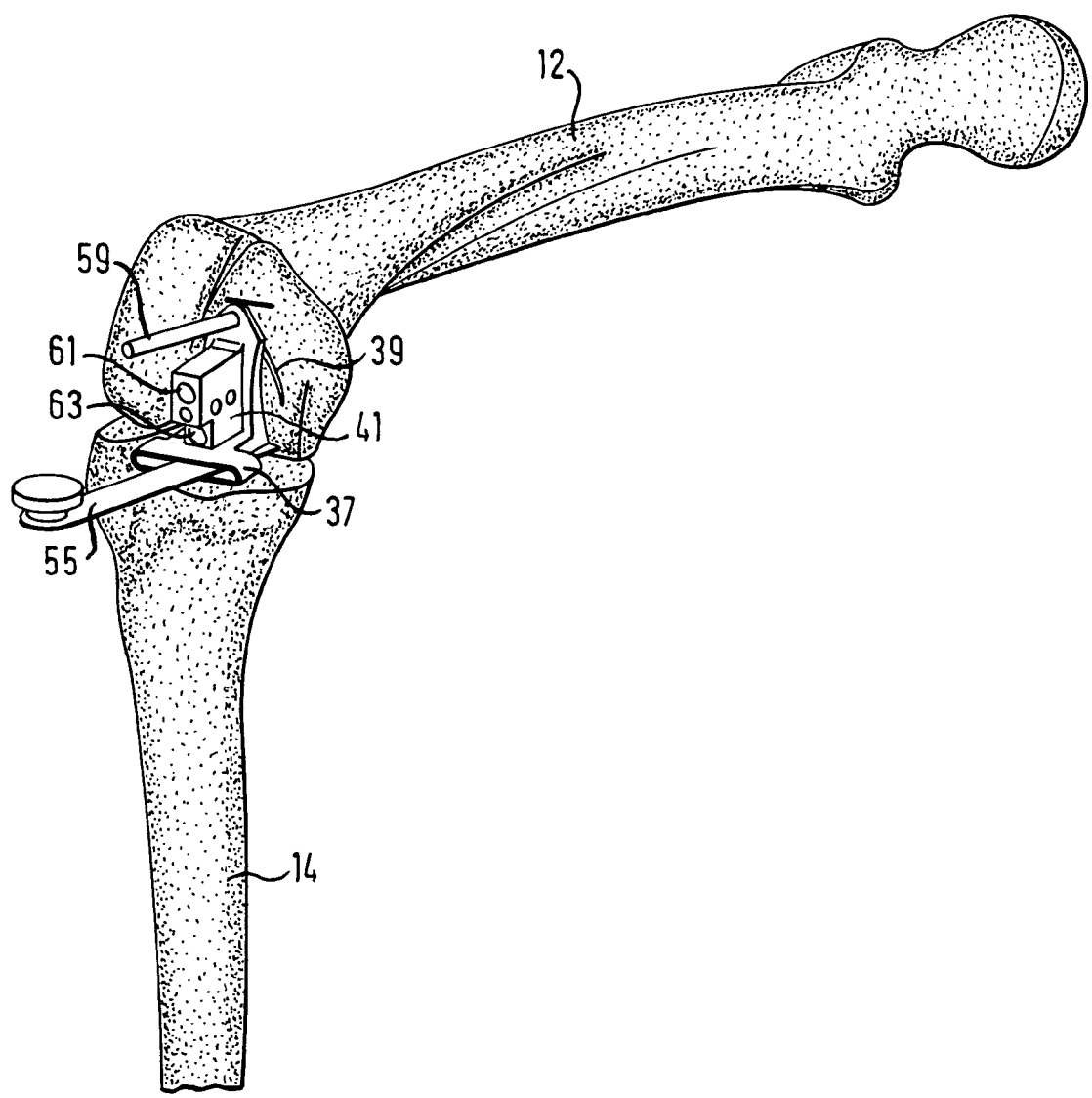

As FIG. 5 shows, the working of the femoral condyle is possible with the knee in flexion without the spreading device 11 in accordance with the invention which can be taken off as soon as the combined cutting and drilling jig 45 is fixed to the femoral condyle. However, it is the spreading device 11 in accordance with the invention which permits a correct positioning both in extension and in flexion of the respective functional section 13, and thus of the respective jig 35, 45, with this taking place with the knee spread open and thus adopting its natural position.

In accordance with FIG. 6, the lower part 17 of the spreading device 11 in accordance with the invention includes a spreading tongue 27 with which the spreading device 11 can be supported on the tibia plateau. A base section 31 of the lower part 17 extends obliquely to the spreading tongue 27 and two passages serving jointly as a guide 25 for the upper part not shown in FIG. 6 are formed therein and extend perpendicular to the spreading tongue 27.

An adjustable screw 21 serving as an actuation member for the spreading device 11 extends through the base section 31 parallel thereto. The base section 31 and the adjustable screw 21 cooperate via a thread 77 such that a pressure surface 23 formed at the free end of the adjustable screw 21 and extending parallel to the spreading tongue 27 is vertically adjustable relative to the spreading tongue 27 by rotating the adjustable screw 21.

The base section 31 of the lower part moreover formed for coupling with the functional attachments 13 has a series 79 of fixing recesses with which the fixing device 49 for the respective functional attachment (cf. FIGS. 8 and 10) can be brought into engagement to fix the functional attachment 13 to the lower part 17. A spring-loaded latch member 81 of the lower part 17 cooperates in each case with a series 83 of latch recesses formed on the functional attachments 13. Lateral guide projections 85 of the lower part 17 engage into lateral grooves 87 of the functional attachments 13, whereby a compulsory guide for the functional attachments 13 is achieved on the adjustment of the functional attachments 13 relative to the spreading device 11.

The functional attachments 13 are consequently not continuously adjustable at the lower part 17 of the spreading device 11, but only the discrete configurations pre-determined by the mentioned fixing and latching means can be set which correspond to the different thicknesses of the available tibia implants.

The spreading device described in this embodiment is used in conjunction with such implant sets in which only the thickness of the tibia implants varies, but the thickness of the femur implants is constant. The setting of the position of the functional attachments 13 relative to the spreading device 11 and thus to the height of the respective cutting jig 35 or 37 over the tibia plateau thus only takes place in dependence on the thickness of the respective tibia implant provided in accordance with the surgery plan. This thickness can be read off at a scale 33 formed at the lower part 17 when the functional attachment 13 is coupled to the spreading device 11.

The upper part 19 of the spreading device 11 shown in FIG. 7 includes a spreading tongue 29 which extends perpendicular to two guide rods 65 with which the upper part 19 is plugged into the guide passages 25 of the lower part 17.

FIG. 8 shows the functional attachment 13 used in extension whose head section 51 is formed as a cutting jig 35 provided with a slot 53 for a saw blade for the carrying out of the first condylar cut (cf. FIG. 3).

The lateral guide grooves 87 and the series of latch recesses 83 are formed at a body section 47 of the functional attachment 13 extending obliquely to the slot 53. Furthermore, the fixing device 49 is attached to the body section 47 and engages with the free end of a fixing pin 89 into the fixing recesses 79 formed at the lower part 17 of the spreading device 11 when the fixing device 49 is actuated accordingly to fix the functional attachment 13 to the spreading device 11.

FIG. 9 shows the apparatus in accordance with the invention in the assembled state for use when the knee is in extension, i.e. with the functional attachment 13 in accordance with FIG. 8 for the carrying out of the first condylar cut 39.

The spreading tongues 27, 29 of the lower part 17 and of the upper part 19 extend parallel to one another. The region at which the pressure surface 23 (cf. FIG. 6) of the actuation member 21 acts on the lower side of the spreading tongue 29 of the upper part 19 is offset by an amount a different from zero, such as is indicated in FIG. 9, perpendicular to the spreading direction, i.e. parallel to planes fixed by the spreading tongues 27, 29, with respect to the guide axis fixed by the guide passages 25 of the lower part 17 and extending parallel to the spreading direction for each position of the actuation member 21. No canting of the guide rods 65 of the upper part 19 hereby arises in the guide passages 25 of the lower part 17 when the adjustable screw 49 is actuated.

Furthermore, the advantageous design of the apparatus in accordance with the invention with the angle α exceeding 90° between the spreading section including the spreading tongues 27, 29 and the handling section including the base section 31 and the actuation member 21.

In the functional attachment 13 shown in FIG. 10 and used for the preparation of the femoral condyle with the knee in flexion (cf. FIGS. 4 and 5), the head section 51 is made as a support for the combined cutting and drilling jig 45 shown in FIG. 11. The head section 51 has a coupling rail 91 which is T shaped in cross-section and onto which the jig 45 can be pushed via a section made as a sliding attachment shoe. Spring-loaded latch heads 67 which are each attached at both sides to the ends of the coupling rail 91 of the head part 51 serve as abutments which can be overcome.

The combined cutting and drilling jig 45 provided in different sizes corresponding to a set of existing femur implants is formed in the lower region as a cutting jig 37 provided with a slot 57 for a saw blade and in the upper region as a drilling jig 41 which is provided with two fixing passages 69 and through which in each case a drill can be guided for the pre-drilling of the bone and subsequently a fixing element, in particular a bone screw, can be guided to fix the jig 45 to the bone.

As already mentioned above, the jig 45 corresponds with respect to the curvature to its concave side 71 facing the femoral condyle during the operation and with respect to the position and to the orientation of the fixing passages 69 with regard to the curved side 71 to a femur implant of the same size. In this respect, the femur implant to be inserted is simulated by means of the jig 45 in the operation.

At its upper end, the jig 45 is provided with a positioning passage 75 through which the positioning pin 59 (cf. e.g. FIG. 5) is guided to hold the jig 45 at the femoral condyle, while the bores for the fixing screws 61, 63 or for the spigots of the femur implant to be inserted are carried out via the fixing passages 69 in the femoral condyle.

Furthermore, the jig 45 is provided in the region between the two fixing passages 69 with transversely extending coupling passages 73 which jointly serve as a coupling section via which the jig 45 can be coupled to further instruments, in particular to alignment aids, manipulation devices and further cutting jigs.

REFERENCE NUMERAL LIST 11 spreading device
12 femur
13 functional attachment
14 tibia
17 lower part
19 upper part
21 actuation member, adjustable screw
23 pressure surface
25 guide
27 spreading tongue of the lower part
29 spreading tongue of the upper part
31 base section of the lower part
33 display device, scale
35 cutting jig for extension
37 cutting jig for flexion
39 first condylar cut, first cut surface
41 drilling jig for flexion
45 combined cutting and drilling jig
47 body section of the functional attachment
49 fixing device
51 head section of the functional attachment
53 slot for extension
55 cutting tool, saw blade
57 slot for flexion
59 positioning pin
61 fixing element, screw
63 fixing element, screw
65 guide rod
67 latch head
69 fixing passage
71 curved side
73 coupling passage
75 positioning passage
77 thread
79 series of fixing recesses
81 latch member
83 series of latch recesses
85 guide projection 87 lateral guide groove
89 fixing pin
91 coupling rail
a offset
α angle between the spreading section and the handling section

The invention claimed is:

1. An apparatus for the preparation of a femoral condyle for the insertion of monocondylar knee implants, comprising:
   a spreading device (11) for the setting of a desired spacing between a femoral condyle and an oppositely disposed tibia plateau and comprising at least one functional attachment (13) couplable in a vertically adjustable manner with the spreading device (11),
   wherein the spreading device (11) includes a spreading section (27, 29), which can be introduced between the femoral condyle and the tibia plateau and which extends substantially perpendicular to the spreading direction, and a handling section (21, 31) for the spreading section (27) which includes an angle α>90° with the spreading section (27, 29),
   wherein the functional attachment (13) supports a cutting and/or drilling jig (35, 45) and is adjustable at least vertically relative to the spreading device (11) when the desired spacing is set at the handling section (21, 31) by means of the spreading device (11),
   wherein the spreading device (11) includes a lower part (17) supportable at the tibia plateau, an upper part (19) adjustably guided at the lower part (17) and an actuation member (21) adjustably held at the lower part (17) which cooperates with the lower part (17) and the upper part (19) such that a setting movement of the actuation member (21) can be translated into a spreading movement of the upper part (19) away from the lower part (17), and
   wherein the actuation member (21) is provided at its free end with a pressure surface (23) which extends parallel to a lower side of the upper part (19) which can be acted on by means of the pressure surface (23).

2. An apparatus in accordance with claim 1, wherein the upper part (19) is able to be acted on from below via the actuation member (21) and can be pressed away from the lower part (17) in the spreading direction.

3. An apparatus in accordance with claim 1, wherein the actuation member (21) is adjustable obliquely to the spreading direction and the upper part (19) is adjustable parallel to the spreading direction relative to the lower part (17).

4. An apparatus in accordance with claim 1, wherein the lower part (17) and the upper part (19) each have a plate-shaped spreading tongue (27, 29) with which the lower part (17) is supported at the tibia plateau and the upper part (19) can be pressed toward the femoral condyle.

5. An apparatus in accordance with claim 4, wherein the actuation member (21) is drivable into an intermediate space between the two spreading tongues (27, 29) and toward the lower side of the spreading tongue (29) of the upper part (19), with the lower part (17) including a base section (31) which extends obliquely to its spreading tongue (27) and in which the guide (25) for the upper part (19) is formed and the actuation member (21) is held.

6. An apparatus in accordance with claim 1, wherein the spreading device (11) is provided with a display device (33) by means of which a desired height of the functional attachment (13) dependent on the thickness of the tibia implant to be inserted can be read off at the spreading device (11).

7. An apparatus in accordance with claim 1, wherein the functional attachment (13) is adjustable between discrete positions relative to the spreading device (11) which are spaced apart corresponding to the thicknesses of a set of tibia implants of different thickness.

8. An apparatus in accordance with claim 1, wherein the spreading device (11) is movable relative to the knee in the condition arranged between the tibia plateau and the femoral condyle, substantially displaceable perpendicular to the spreading direction and/or rotatable about an axis extending substantially parallel to the spreading direction.

9. An apparatus in accordance with claim 1, wherein the spreading device (11) is couplable to a plurality of differently formed functional attachments (13).

10. An apparatus in accordance with claim 1, wherein at least one functional attachment (13) is made as a cutting jig (35) for fixing the position of a condylar cut (39) which is to be carried out when the knee is in extension and which extends substantially parallel to the tibia plateau.

11. An apparatus in accordance with claim 1, wherein at least one functional attachment (13) is made as a cutting jig (37) for fixing the position of a condylar cut which is to be carried out when the knee is in flexion and which extends substantially parallel to the tibia plateau.

12. An apparatus in accordance with claim 1, wherein at least one functional attachment (13) is made as a drilling jig (41) for fixing the position of at least one condylar bore which serves for the fixing of a femur implant, which is to be carried out when the knee is in flexion and extends substantially parallel to the tibia plateau.

13. An apparatus in accordance with claim 1, wherein at least one functional attachment (13) is made as a combined cutting and drilling jig (45) for the simultaneous fixing of the position of a condylar cut and of at least one condylar bore when the knee is in flexion.

14. An apparatus in accordance with claim 1, wherein at least one functional attachment (13), which is formed as a combined cutting and drilling jig (45), can be fixed to the femoral condyle.

15. An apparatus in accordance with claim 1, wherein the functional attachment (13) includes a body section (47) extending obliquely to the spreading direction in the state coupled to the spreading device (11), couplable to the spreading device (11) and having a fixing device (49) and a head section (51) fixedly connected to the body section (47) which is formed as a cutting and/or as a drilling jig (35) or as a support for a separate cutting and/or drilling jig (45).

16. An apparatus in accordance with claim 15, wherein the head section (51) is made as a cutting jig (35) with a slot (53) for a cutting tool (55) defining a cutting plane and extending perpendicular to the spreading direction in the state coupled to the spreading device (11).

17. An apparatus in accordance with claim 15, wherein the head section (51) is made as a support for a separate cutting and/or drilling jig (45) which can be releasably connected to the head section (51) and which can be fixed to the femoral condyle when the knee is in flexion.

18. An apparatus in accordance with claim 17, wherein the cutting and/or drilling jig (45) is adjustable along the head section (51) in the state connected to the head section (51).

19. An apparatus in accordance with claim 1, wherein at least one functional attachment (13), which is made as a combined cutting and drilling jig (45) can be coupled to an additional cutting jig which is made for fixing the position of a further condylar cut, when the knee is in flexion, with the further condylar section extending in a curved manner between two planar cut surfaces (39) previously made at the femoral condyle.

20. An apparatus for the preparation of a femoral condyle for the insertion of monocondylar knee implants, comprising:

a spreading device (11) for the setting of a desired spacing between a femoral condyle and an oppositely disposed tibia plateau and comprising at least one functional attachment (13) couplable in a vertically adjustable manner with the spreading device (11), wherein the spreading device (11) includes a spreading section (27, 29), which can be introduced between the femoral condyle and the tibia plateau and which extends substantially perpendicular to the spreading direction, and a handling section (21, 31) for the spreading section (27) which includes an angle α>90° with the spreading section (27, 29), wherein the functional attachment (13) supports a cutting and/or drilling jig (35, 45) and is adjustable at least vertically relative to the spreading device (11) when the desired spacing is set at the handling section (21, 31) by means of the spreading device (11), wherein the spreading device (11) includes a lower part (17) supportable at the tibia plateau, an upper part (19) adjustably guided at the lower part (17) and an actuation member (21) adjustably held at the lower part (17) which cooperates with the lower part (17) and the upper part (19) such that a setting movement of the actuation member (21) can be translated into a spreading movement of the upper part (19) away from the lower part (17), and wherein a guide (25) for the upper part (19) extending parallel to the spreading direction and the region at which the actuation member (21) acts on the upper part (19) are offset with respect to one another perpendicular to the spreading direction.

* * * * *